(12) United States Patent
Shefer et al.

(10) Patent No.: US 7,115,282 B2
(45) Date of Patent: Oct. 3, 2006

(54) MULTI COMPONENT CONTROLLED RELEASE SYSTEM FOR ANHYDROUS COSMETIC COMPOSITIONS

(75) Inventors: Adi Shefer, East Brunswick, NJ (US); Shmuel David Shefer, East Brunswick, NJ (US)

(73) Assignee: Salvona IP LLC, Dayton, NJ (US)

( * ) Notice: Subject to any disclaimer, the term of this patent is extended or adjusted under 35 U.S.C. 154(b) by 0 days.

(21) Appl. No.: 10/124,207

(22) Filed: Apr. 17, 2002

(65) Prior Publication Data

US 2003/0198652 A1 Oct. 23, 2003

(51) Int. Cl.
*A61K 9/16* (2006.01)
*A61K 9/14* (2006.01)
*A61K 6/00* (2006.01)

(52) U.S. Cl. ............. 424/490; 424/401; 424/489; 424/491; 424/493; 424/496

(58) Field of Classification Search ............. 424/401, 424/408, 450, 451, 457, 463, 484, 486, 489, 424/490, 493, 494, 491, 496–498
See application file for complete search history.

(56) References Cited

U.S. PATENT DOCUMENTS

| | | | |
|---|---|---|---|
| 3,971,852 A | | 7/1976 | Brenner et al. ............ 426/103 |
| 4,264,586 A | * | 4/1981 | Callingham et al. .......... 424/68 |
| 5,628,990 A | * | 5/1997 | Murphy et al. ............. 424/65 |
| 5,783,211 A | * | 7/1998 | Manzo et al. ............. 424/450 |
| 5,945,095 A | | 8/1999 | Mougin et al. ......... 424/78.02 |
| 6,045,823 A | * | 4/2000 | Vollhardt et al. .......... 424/450 |
| 6,309,655 B1 | * | 10/2001 | Minnix ...................... 424/401 |
| 6,387,398 B1 | * | 5/2002 | Vollhardt et al. .......... 424/450 |
| 2003/0099678 A1 | * | 5/2003 | Maibach et al. ............ 424/401 |
| 2003/0113540 A1 | * | 6/2003 | Anderson et al. .......... 428/403 |

FOREIGN PATENT DOCUMENTS

| | | | |
|---|---|---|---|
| EP | 0 908 174 A2 | | 4/1999 |
| EP | 908174 A2 | * | 4/1999 |
| WO | WO 9828398 A1 | * | 7/1998 |
| WO | WO 0209663 | * | 2/2002 |

* cited by examiner

*Primary Examiner*—S. Tran
(74) *Attorney, Agent, or Firm*—Mathews, Shepherd, McKay & Bruneau, P.A.

(57) ABSTRACT

The present invention relates to an improved controlled release system that can be incorporated into anhydrous cosmetic formulations and can encapsulate different types of fragrances, flavors, active ingredients, or combinations of fragrances, flavors, and various active ingredients. The controlled delivery system of the present invention is substantially free-flowing powder formed of solid hydrophobic nano-spheres that are encapsulated in a moisture sensitive micro-spheres. The fragrances, flavors, and active ingredients encapsulated in the nano-spheres can be the same or different from those encapsulated in the micro-sphere. The encapsulation of one or more fragrances, flavors or active agents in the various components of the system, such as nano-spheres and micro-spheres, provides odor or flavor transition (change in odor character or change in flavor character) during the use of the product, in response to moisture, such as wetting the lips, perspiration, and the like. The incorporation of the controlled release system of the present invention into anhydrous cosmetic formulations was found to provide moisture triggered release, as well as prolonged release of the fragrances, flavors, and active ingredients that are encapsulated in the solid hydrophobic nano-spheres over an extended period of time.

19 Claims, 1 Drawing Sheet

MULTI COMPONENT CONTROLLED RELEASE SYSTEM FOR ANHYDROUS COSMETIC COMPOSITIONS

BACKGROUND OF THE INVENTION

1. Field of the Invention

The present invention relates to an improved controlled release system that can be incorporated into anhydrous cosmetic formulations such as powders, sticks, and sprays that provides moisture triggered release, fragrance or flavor transition, as well as, prolong release of fragrances, flavors, and other active ingredients onto the target site over an extended period of time.

2. Description of the Related Art

The cosmetic industry has searched many years for ways to enhance the performance of consumer and diversified products and make them more aesthetically pleasing for the consumers. Consumer acceptance of cosmetic products is determined not only by the performance achieved with these products but the aesthetics associated therewith. Fragrances and flavors are an important aspect of the successful cosmetic products and they are being utilized, in addition to imparting an aesthetically pleasing odor, or a taste, to convey to the consumer the product performance and effectiveness.

Consumers are becoming increasingly educated and expect a high level of sophistication in their cosmetic products and the cosmetic market has become extremely competitive. Many consumers would prefer for the fragrance, or the flavor present in these products, to be remained on the area of application for an extended period of time. Also, there is a need for a controlled release system that will provide a signal, such as a change in odor character, or flavor character, upon activation of the product or to signal that a new application is needed. There is also a need for controlled release systems that provide special performance features to differentiate the product from that of the competitor.

U.S. Pat. No. 3,971,852 discloses the use of spray-dried particles of starch derivatives, natural gums (e.g., gum arabic), and polyhydroxy compounds (i.e., mannitol, sorbitol) in cosmetic, personal care, and household products. The drawback of these types of materials is the relatively large amount of surface oil, sometimes up to 12%. As a result, the retention of volatile fragrance ingredient may be poor leading to premature leaking of the fragrance. These types of materials, also quickly release the fragrance, or other active ingredients that are encapsulated within their structure upon exposure to water, and would not have the ability to extend the release of fragrances, flavors, and other active ingredients over an extended period of time.

U.S. Pat. No. 5,945,095 discloses a composition, in particular a cosmetic, dermatological, hygiene or pharmaceutical composition, to care for and/or make up the skin, which composition may be in the form of a compact powder or a cast product, comprising a dispersion of polymer particles in a fatty substance. Furthermore, the invention relates to the use of this dispersion in such a composition.

A controlled release system for cosmetic and pharmaceutical products based on spray-dried multilamellar phospholipid liposomes is disclosed in U.S. Pat. Nos. 5,783,211 and 6,045,823. The liposomes encapsulate a biologically active agent is selected from the group consisting of anti-inflammatory, antiphlogistic, antibacterial, antiperspirant, astringent, and anti-fungal agents. The problems with using liposomes and structured vesicles as delivery devices are manifold. These types of systems are unstable, and can only be used for encapsulation of certain types of materials. The liposomes disclosed in U.S. Pat. Nos. 5,783,211 and 6,045,823 are released in response to moisture but are not able to sustain the release of the active agents over an extended period of time because liposomes are is not stable. The problems with using the liposomes and structured vesicles that are disclosed in disclosed in U.S. Pat. Nos. 5,783,211 and 6,045,823 as delivery systems, are that these types of systems are very dynamic, unstable in aqueous compositions, and can only be used for encapsulation of certain types of materials. Stability has become the major problem limiting the use of liposomes for controlled delivery, both in terms of shelf life and after administration.

The prior art of which applicant is aware does not set forth a controlled release system that comprises of solid hydrophobic nano-spheres encapsulated in a moisture sensitive micro-sphere that can be incorporated in anhydrous cosmetic formulations such as powders, sticks, and sprays (i.e., deodorant body powders, lip bahns, lip sticks, make-up sticks, and underarm deodorant or antiperspirant sticks, body sprays, foot spray, hygiene sprays, feminine napkin sprays, undergarment sprays, etc.) and can encapsulate one or more different fragrances, flavors, or combinations of fragrances, flavors, and various active ingredients.

SUMMARY OF THE INVENTION

The present invention relates to a novel controlled release system comprising of solid hydrophobic nano-spheres encapsulated in a water sensitive micro-sphere that can be incorporated into anhydrous cosmetic formulations such as powders, sticks, and sprays, such as deodorant body powders, lip balms, lipsticks, make-up sticks, and underarm deodorant or antiperspirant sticks, body sprays, foot spray, hygiene sprays, feminine napkin sprays, undergarment sprays, and the like, and can encapsulate one or more types of fragrances, flavors, or combinations of fragrances, flavors, and various active ingredients. The different fragrances, flavors, and the active ingredients can be incorporated in the hydrophobic nano-sphere matrix, in the water sensitive micro-sphere matrix, or in both the nano and micro spheres matrices. The controlled release system of the present invention provides moisture-triggered release of the actives that are encapsulated in the micro-sphere matrix, as well as, prolong release of the actives encapsulated that are encapsulated in the nano-sphere matrix over an extended period of time.

The micro-spheres have an average sphere size in the range from about 20 microns to about 100 microns. The nano-sphere have an average sphere size in the range from about 0.01 micron to about 5 microns and having a melting point in the range from about 30 degrees C. to about 90 degrees C. A first fragrance, flavor, or active ingredient can be encapsulated in a water sensitive micro-sphere and released upon exposure of the system to moisture (wetting the lips, perspiration, and the like) and a second fragrance, flavor, or active ingredient can be encapsulated in the solid hydrophobic nano-spheres and released over an extended period of time. In addition, the production of the controlled release system utilizes minimum processing steps and is efficient and economical.

The carrier system of the present invention is a free-flowing powder formed of solid hydrophobic nano-spheres comprising fragrances, flavors, and other various active ingredients, that are encapsulated in a moisture sensitive micro-spheres that can also contain fragrances, flavors, and other various active ingredients. The active ingredients encapsulated in the nano-spheres can be the same or different from those encapsulated in the micro-sphere. The controlled release system of the present invention is characterized by:

(i) protection of the active ingredients, as well as the volatile constituents of the fragrances or flavors, during storage, until needed;
(ii) moisture triggered release of the fragrances, flavors, and other active ingredients that are encapsulated in the micro-sphere water sensitive matrix, as well as, the nano-spheres comprising the same or other fragrances, flavors, and active ingredients (upon wetting the lips, upon perspiration, etc.);
(iii) change in odor character or change in flavor character in response to moisture; and
(iv) prolonged release of fragrances, flavors, and other active ingredients that are encapsulated in the solid hydrophobic nano-spheres, over an extended period of time.

The present invention also provides a method for producing the multi component controlled release system for an anhydrous composition comprising the steps of:

(i) incorporating the fragrance, flavor, and other active ingredients into the solid hydrophobic nano-spheres;
(ii) forming an aqueous mixture comprising of one or more fragrance, flavor, and other active ingredients, the nano-spheres, and a water sensitive material, such as, starch derivatives, natural gums, polyvinyl alcohol, proteins, hydrocolloids, or mixture of thereof; and
(iii) spray drying the mixture to form a dry powder composition.

The invention further provides a process for producing the multi component controlled release system for an anhydrous composition including the fragrances, flavors, and other active ingredients comprising the steps of:

(i) heating one or more hydrophobic materials to a temperature above the melting point of the materials to form a melt;
(ii) dissolving or dispersing a first fragrance or flavor into the melt;
(iii) dissolving or dispersing a first one or more active ingredients into the melt;
(iv) dissolving or dispersing a second fragrance or flavor, active ingredients, and moisture sensitive materials, such as, starch derivatives, natural gums, polyvinyl alcohol, proteins, hydrocolloids, or mixture of thereof, in the aqueous phase;
(v) heating the composition to above the melting temperature of the hydrophobic materials; mixing the hot melt with the aqueous phase to form a dispersion;
(vi) high shear homogenization of the dispersion at a temperature above the melting temperature until a homogeneous fine dispersion is obtained having a sphere size of from about 1 micron to about 2 microns;
(vii) cooling the dispersion to ambient temperature; and
(viii) spray drying the emulsified mixed suspension to form a dry powder composition.

The incorporation of spray dried nano-spheres comprising fragrances, flavors, and other active ingredients encapsulated within a moisture sensitive matrix into anhydrous cosmetic formulations was found to provide fragrance or flavor transition (change in odor character or change in flavor character) in response to moisture. Furthermore the system was found to extend the release rate of the fragrances, flavors, and the active ingredients that were encapsulated in the solid hydrophobic nano-spheres over an extended period of time. In an alternate embodiment, a controlled release composition for an anhydrous composition is formed of hydrophobic nano-spheres incorporating active agents.

The invention also provides anhydrous cosmetic formulations such as powders, sticks, and sprays (i.e., deodorant body powders, lip balms, lipsticks, make-up sticks, and underarm deodorant or antiperspirant sticks, body sprays, foot spray, hygiene sprays, feminine napkin sprays, undergarment sprays, etc.) comprising the controlled release system of the present invention. Skin or lips treated with anhydrous cosmetic formulations (i.e., deodorant body powders, lip balms, lipsticks, make-up sticks, and underarm deodorant or antiperspirant sticks, body sprays, foot spray, hygiene sprays, feminine napkin sprays, undergarment sprays, etc.) comprising the controlled release system of the present invention were observed to provide fragrance or flavor transition (change in odor character or change in flavor character) in response to moisture (wetting the lips, perspiration, etc.) and fragrance perception, or flavor perception, on the target site has been observed to be perceived over an extended period of time, such as a few hours.

The multi-component controlled release system of the present invention can comprise from about 1% to about 50% by weight of a hydrophobic matrix, from about 1% to about 50% by weight of a water sensitive matrix, and from about 1% to about 50% by weight is fragrance, flavor, or other active ingredients.

The present invention addresses the foregoing need for cosmetic products that provide special performance features to enhance product performance and differentiate the product from that of the competitors and provide long-term storage stability. The invention will be more fully described by reference to the following drawing.

DETAILED DESCRIPTION

Figure 1:
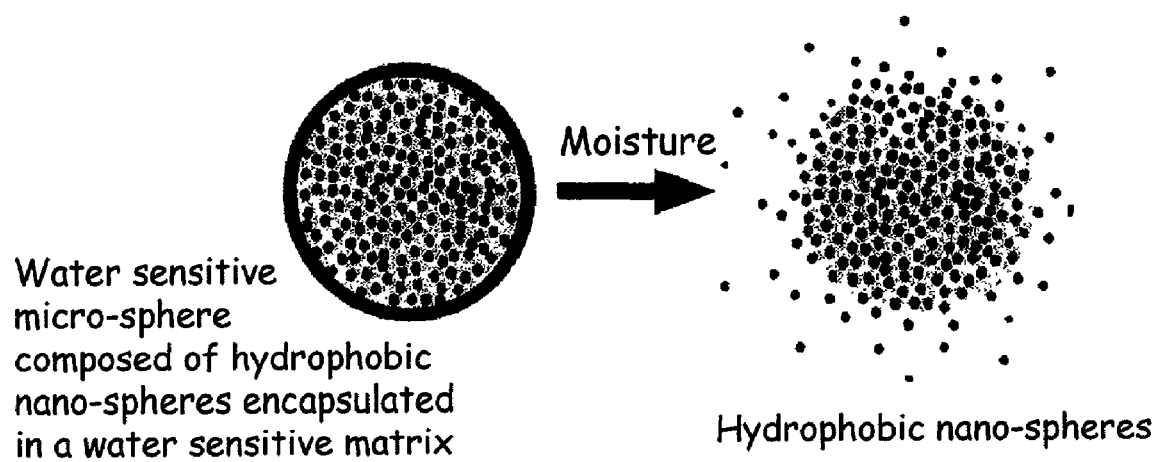
FIG. 1. is a schematic diagram of a controlled release system of the present invention.

The present invention provides a method to enhance the performance of anhydrous compositions such as cosmetic formulations. The invention relates to a controlled release system that provides odor or flavor transition (change in odor character or change in flavor character) during the use of the product, in response to moisture (wetting the lips, perspiration, and the like) and extends fragrance or flavor perception on the target site.

The controlled release system of the present invention is a free-flowing powder formed of solid hydrophobic nano-spheres comprising one or more of fragrances, flavors, and active ingredients that are encapsulated in a moisture sensitive micro-sphere that can also encapsulate the same or other fragrances, flavors, and active ingredients, as shown in FIG. 1. The term "spheres" is intended to describe solid, substantially spherical particulates. It will be appreciated that other shapes can be formed in accordance with the teachings of the present invention.

The nano-spheres of the present invention have an average diameter in the range from about 0.01 micron to about 10 microns. Preferably, the sphere size of the nano-spheres is in the range from about 0.05 microns to about 2 microns. This linear dimension for any individual sphere represents the length of the longest straight line joining two points on the surface of the sphere.

Additional cosmetic, dermatological, and pharmaceutical active agents can be added to the controlled release system of the present invention including, but are not limited to: anti-oxidants; free radical scavengers; moisturizers; depigmentation agents; reflectants; humectants; antimicrobial (e.g., antibacterial) agents; allergy inhibitors; anti-acne agents; anti-aging agents; anti-wrinkling agents, antiseptics; analgesics; keratolytic agents; anti-inflammatory agents; fresheners; healing agents; anti infectives; inflammation inhibitors; wound healing promoters; peptides, polypeptides and proteins; deodorants and antiperspirants; skin emollients and skin moisturizers; tanning agents; skin lightening agents; antifungals; depilating agents; counterirritants; poison ivy products; poison oak products; bum products; make-up preparations; vitamins; amino acids and their derivatives; herbal extracts; sensory markers (i.e., cooling agents, heating agents, etc.); skin conditioners; chelating agents; cell turnover enhancers; coloring agents; sunscreens; nourishing agents; moisture absorbers; sebum absorbers and the like; skin penetration enhancers; and other active ingredients. The additional components are usually present in an amount from about 1% to about 20% by weight of the spheres.

I. Matrix Materials for Forming the Nano-Spheres

Hydrophobic Matrix Materials

Suitable solid core materials for forming the nano-spheres of the present invention are inert nontoxic hydrophobic materials with a melting point range between about 30 degrees C. and about 90 degrees C. Examples of hydrophobic materials include natural, regenerated, or synthetic waxes including animal waxes such as beeswax, lanolin and shellac wax, vegetable waxes such as carnauba, candelilla, sugar cane, rice bran, and bayberry wax, mineral waxes such as petroleum waxes including paraffin and microcrystalline wax, and mixtures thereof. Other hydrophobic materials which can be used in the present invention include wax and silicon copolymers, such as candelilla wax and silicone copolymer, ozokrite wax and silicon copolymers, beeswax and silicon copolymers, and the like. Other hydrophobic compounds which can be used in the present invention include: fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol, solid hydrogenated castor and vegetable oils, hard paraffins, hard fats, and mixtures thereof. Other hydrophobic compounds which can be used, include triglycerides, preferably of at least food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–18), denoted medium chain triglycerides (MCT). The fatty acid moieties of such triglycerides can be unsaturated or polyunsaturated and mixtures of triglycerides having various fatty acid material. The nano-sphere matrix can comprise a single hydrophobic material or a mixture of a plurality of materials. Other hydrophobic materials that are known to those skilled in the art and suitable materials as described in "Industrial Waxes," Vol. I and II, by Bennett F.A.I.C., published by Chemical Publishing Company Inc., 1975 and Martindale, "The Extra Pharmacopoeia", The Pharmaceutical Press, 28$^{th}$ Edition pp.1063–1072, 1982 can be used in the present invention.

Other hydrophobic compounds which can be used in the present invention include synthetic polymers, such as alkylated polyvinylpyrrolidines, the Ganex® copolymer series, and ProLipid® 151, commercially available from the ISP Company. Examples of other suitable hydrophobic polymers and copolymer for use as the matrix material include polyethylene homopolymers A-C® 1702; A-C® 617, A-C® 617A, and A-C® 15, commercially available from Allied Signal Inc.; PERFORMALENE™ PL commercially available from New Phase Technologies; ETHYLENE-ACRYLIC ACID COPOLYMERS A-C® 540, A-C® 540A, and A-C® 580 commercially available from Allied Signal Inc.; polyamides having a molecular weight in the range of from about 6,000 up to about 12,000, for example, MACROMELT™ 6030 manufactured by the Henkel Ag. of Dusseldorf, Germany; VERSALON™ 1135 polyamide polymer available commercially from General Mills, Inc The nano-spheres of the present invention can have a melting point in the range from about 30 degrees C. to about 90 degrees C., preferably from about 40 degrees C. to about 90 degrees C. The melting point of the spheres is usually a function of the carrier matrix employed. Accordingly, preferred matrix materials have a melting point in the range of about 50 degrees C. to about 80 degrees C., preferably from about 60 degrees C. to about 70 degrees C. It should be understood that it is the melting point of the sphere rather than of the carrier matrix that is important for use of the carrier system of the present invention.

Considerations in the selection of the matrix material include good barrier properties to the active agents and the fragrance ingredients, low toxicity and irritancy, stability, and high loading capacity for the active agents of interest.

II. Matrix Materials for Forming the Micro-Spheres

Water Sensitive Materials

Water-sensitive materials for forming the micro-spheres of the present invention comprise water soluble and water dispersible synthetic polymers and copolymers, starch derivatives, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

Polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I-XIV of U.S. Pat. No. 5,051,222 issued on Sep. 24, 1991, the specification for which is incorporated by reference herein.

A polyvinyl alcohol useful for practice of the present invention is Mowiol® 3-83, having a molecular weight of about 14,000 Da and degree of hydrolysis of about 83%, Mowiol® 3-98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.; ELVANOL® 51-05, having a molecular weight of about 22,000–26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9-6, Nozaki Cho, Kita-Ku, Osaka, 530 Japan.

Suitable polysaccharides are polysaccharides of the non-sweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

III. Fragrances, Flavors and Active Ingredients

Fragrances and flavors can be included in the controlled system of the present invention. The fragrances and flavors that can be encapsulated in the system of the present invention can be any odoriferous or flavor material and can be selected according to the desires of the fragrance or flavor creator. In general terms, such fragrance and flavor materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery and flavor uses, including materials such as aldehydes, ketones, esters, and the like. More commonly, naturally occurring plant and animal oils and exudates comprising complex mixtures of various chemical components are known for use as fragrances or flavors and such materials can be used herein. Fragrances and flavors useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention comprise, for example the high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to fabrics. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

IV. Processing Method

IVa. Nano-Spheres

The encapsulated fragrances, flavors, and active ingredients in the nano-spheres of the present invention can be prepared by the steps of (1) heating hydrophobic materials to a temperature above the melting point to form a melt, (2) dissolving or dispersing the first said fragrance, flavor, and first said active ingredients in the melt, (4) emulsifying the melt in the aqueous phase; and (5) cooling the dispersion to ambient temper to form a fine suspension.

The fragrances, flavors, other active ingredients can be incorporated into the hydrophobic solid nano-spheres. Preferably, about 1% to about 80% of and more preferably about 1% to about 60% by weight of the active ingredients are used in forming the nano-spheres.

IVb. Micro-spheres

The controlled release system of the present invention can be prepared by the steps of (a) incorporating the selected fragrances, flavors, and active ingredients into the hydrophobic interior of the nano-spheres, (b) forming an aqueous mixture comprising one or more fragrance, flavor, and active agents, the nano-spheres, and a water sensitive material, and (c) spray drying the mixture of the present invention to form a dry powder composition. Accordingly, the nano-spheres can be encapsulated into the micro-sphere structure. One or more of the fragrances, flavors, or active ingredients, which can be the same or different than the fragrances, flavors, and active ingredients incorporated in the nano-sphere can be incorporated into the micro-sphere structure.

A process for producing the multi component controlled release system can include the following steps:

(i) heating hydrophobic materials to a temperature above the melting point of the materials to form a melt;
(ii) dissolving or dispersing the first said fragrance or flavor into the melt;
(iii) dissolving or dispersing the first said active ingredients into the melt;
(iv) dissolving or dispersing a second said fragrance or flavor, second said active ingredients, and moisture sensitive materials, such as, starch derivatives, natural gums, polyvinyl alcohol, proteins, hydrocolloids, or mixture of thereof, in the aqueous phase;
(v) heating the composition to above the melting temperature of the hydrophobic materials;
(vi) mixing the hot melt with the aqueous phase to form a dispersion;
(vii) high shear homogenization of the dispersion at a temperature above the melting temperature until a homogeneous fine dispersion is obtained having a sphere size of from about 1 micron to about 2 microns;
(viii) cooling the dispersion to ambient temperature; and
(ix) spray drying the emulsified mixed suspension to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245–265; Barreto, "Spray Dried Perfumes for Specialties, Soap and Chemical Specialties", December 1966; Maleeny, Spray Dried Perfumes, Soap and San Chem, January 1958, pp.135 et seq.; Flinn and Nack, "Advances in Microencapsulation Techniques", Batelle Technical Review, Vo. 16, No.2, pp.2–8 (1967); U.S. Pat. Nos. 5,525,367; and 5,417,153 which are incorporated herein as references.

In the preferred embodiment, the active agent is present at a level from about 0.01% to about 60%, preferably from about 1% to about 50% by weight of the micro-sphere. In the preferred embodiment, the nano-spheres are generally present in the water sensitive matrix at a level from about 1% to about 80%, preferably from about 1% to about 60% by weight of the matrix material with the balance being the fragrances, flavors, other active ingredients, and the water sensitive materials. In the preferred embodiment, the moisture sensitive matrix is generally present at a level from about 1% to about 80%, preferably from about 1% to about 60% by weight of the matrix material with the balance being the fragrances, flavors, other active ingredients, and the hydrophobic materials.

In one embodiment micro-spheres are formed by mixing nano-spheres incorporating a selected active agent with polyvinyl alcohol, or compositions of polyvinyl alcohol and polysaccharides, under conditions sufficient to encapsulate the nano-spheres. Preferably mixing a selected active agent with the polyvinyl alcohol, or compositions of polyvinyl alcohol and polysaccharides, until the emulsion is formed and then spray drying the emulsion to thereby form an encapsulated nano-sphere. In the preferred embodiment, the moisture sensitive matrix is formed of a polyvinyl alcohol material at a level from about 1% to about 80%, preferably from about 1% to about 70% by weight of the matrix material with the balance being the amount by weight of active agents and an optimal amount of polysaccharides. In an alternate embodiment, polyvinyl alcohol is present in the matrix material in an amount of about 1% to about 80% and the weight of the polysaccharides are present in the amount of about 1% to about 80%. In the preferred embodiment, the active agent composition is generally present at a level from about 0.01% to about 80% preferably from about 1% to about 50% by weight of the encapsulated active agent with the balance being the polyvinyl alcohol or polyvinyl alcohol and polysaccharides. Optionally other conventional ingredients known in the art such as preservatives, surfactants, can be used in accordance with the teachings of the present invention. The multi-component spheres of the present invention preferably have size of from about 0.5 micron to about 300 microns, more preferably from about 1 micron to about 200 microns, most preferably from about 2 microns to about 50 microns. The present invention preferably has minimal active agents on the surface of the spheres, preferably less than 1%.

Polyvinyl alcohol is an excellent barrier material to the permeation of the volatile fragrance ingredients, and as a result the controlled release Systems of the present invention do not provide perceptible odor in the dry state. Upon wetting by a sufficient amount of aqueous fluid such as a perspiration, or wetting the lips, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of moisture activated spheres which provide varying rates of diffusion are contemplated. For example, the moisture activated spheres may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

It has been found that a greater amount of polyvinyl alcohol in the matrix provides slower release rate as compared to a matrix including a lesser amount of polyvinyl alcohol in combination with a polysaccharide. For example, a matrix having about 70% to about 80% polyvinyl alcohol has a slower release rate than a matrix having about 30% to about 40% polysaccharide and about 40% to about 50% polyvinyl alcohol. For example, if a high amount of polyvinyl alcohol is used in the matrix, such as in the range of about 70% to about 80%, the matrix provides controlled release of the active agent over an extended period of time from the time the matrix contacts moisture up to forty-eight hours. If polyvinyl alcohol is combined with polysaccharide in the matrix, such as in the amount of 30% to about 40% polyvinyl alcohol and 30% to about 40% of polysaccharide, a greater amount of active agent is released upon contract with moisture to provide a "burst" of the active agent and the active agent is released over a shorter period of time for example from the time the matrix contacts the fluid up to the range of about 6 hours to about twenty-four hours. Typically, the active agent at the surface of the sphere can be released upon contact with the fluid with the remainder of the active agent being either released in a burst if the matrix dissolves or over an extended period of time upon swelling and softening of the matrix.

Nano-spheres formed of a hydrophobic material provide a controlled release system in order to release the active agent over an extended period of time by molecular diffusion. Fragrances, flavors, and other active agents in the hydrophobic matrix of the nano-spheres can be released by transient diffusion. The theoretical early and late time approximation of the release rate of the active ingredients dissolved in the hydrophobic matrix of the nano-spheres can be calculated from the following equations:

Early time approximation $(m_t/m_{sec}) < 0.4$ $$\frac{M_t}{M_\infty} = 4\left(\frac{D_p t}{\Pi r^2}\right)^{1/2} - \frac{D_p t}{r^2} \quad (1)$$

-continued $$\frac{dM_t/M_\infty}{dt} = 2\left(\frac{D_p}{\prod r^2 t}\right)^{1/2} - \frac{D_p}{r^2} \quad (2)$$

Late time approximation
$(m_t/m_{sec}) > 0.6$ $$\frac{M_t}{M_\infty} = 1 - \frac{4}{(2.405)^2}\exp\left(\frac{-(2.405)^2 D_p t}{r^2}\right) \quad (3)$$

$$\frac{dM_t/M_\infty}{dt} = 1 - \frac{4D_p}{r^2}\exp\left(\frac{-(2.405)^2 D_p t}{r^2}\right) \quad (4)$$

wherein:
r is the radius of the cylinder,
m∞ is the amount fragrance released from the controlled release system after infinite time;
$m_t$ is the amount fragrance released from the controlled release system after time t; and
$D_p$ is the diffusion coefficient of the fragrance or aroma chemical in the matrix The release rate for releasing the fragrance, flavor, or other active agents from the hydrophobic nano-spheres is typically slower than the release rate for releasing active agent from the moisture sensitive matrix. The active agents can be selected to be incorporated into either the hydrophobic nano-spheres or the moisture sensitive matrix depending on the desired time for release of the active agents. For example, a predetermined first active agent can be incorporated in the moisture sensitive matrix to be released upon perspiration or wetting the lips and a predetermined second active agent can be incorporated in the hydrophobic nano-spheres for release over an extended period of time during or after the first agent has been released. For example, the moisture sensitive matrix formed in accordance with the present invention can release the first active agent upon contact with moisture to provide a "burst" with continued release of the first active agent and nano-spheres formed in accordance with the present invention can release the active agent depending on the release rate from an initial time such as within few hours, up to a period of few days.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and claims, are by weight and are approximations unless otherwise stated.

PREPARATION OF DUAL FRAGRANCE CONTROLLED RELEASE SYSTEM

EXAMPLE 1

The following procedure is used for the preparation of a controlled release system that provides flavor transition as well as delivers vitamin E for extended period of time. A peppermint flavor and vitamin E are encapsulated in the hydrophobic nano-spheres and a fruity flavor is encapsulated in the water sensitive micro-sphere. The nano-spheres hydrophobic matrix is candelilla wax, commercially available from Strahl & Pitsch Inc. of West Babylon, N.Y. The micro-sphere water sensitive matrix is Hi-Cap™ 100 (commercially available from the National Starch and Chemical Company of Bridgewater, N.J.).

100 grams of candelilla wax is placed in an oven at 80 degrees ° C. and allowed to melt. 1500 grams of deionized water are placed into 1 gallon vessel, fitted with an all-purpose silicon rubber heater (Cole-Palmer Instrument Company). 500 grams of Hi-Cap™ 100 (commercially available from the National Starch and Chemical Company of Bridgewater, N.J.) was added to the water and the aqueous solution is heated to 90 degree C. while mixing it with a propeller mixer. The candelilla wax is removed from the oven and 50 grams of peppermint flavor (commercially available from Noville Inc. of South-Hackensack, N.J.) and 50 grams of vitamin E (commercially available from JEEN International Corporation of Little Fall, N.J.) are mixed into the melt by hand with a glass rod. The flavor/vitamin E/wax mixture is poured into the aqueous solution and the dispersion and 300 grams of a fruity flavor (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 5% peppermint flavor and 5% vitamin E encapsulated in the solid hydrophobic nano-spheres. The controlled release system obtained contains 5% peppermint flavor, 5% vitamin E, 10% candelilla wax, 30% fruity flavor, and 50% water sensitive material.

EXAMPLE 2

The following procedure is used for the preparation of a controlled release system that provides flavor transition as well as releases a cooling agent for extended period of time. A cooling agent (WS-3 commercially available from Millennium Specialty Chemicals, of Jacksonville, Fla.) is encapsulated in the hydrophobic nano-spheres and a fruity flavor (commercially available from Noville Inc. of South-Hackensack, N.J.) is encapsulated in the water sensitive micro-sphere. The nano-spheres hydrophobic matrix is candelilla wax, commercially available from Strahl & Pitsch Inc. of West Babylon, N.Y. The micro-sphere water sensitive matrix is Hi-Cap™ 100 (commercially available from the National Starch and Chemical Company of Bridgewater, N.J.).

150 grams of candelilla wax is placed in an oven at 80 degrees C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. The candelilla wax is removed from the oven and 100 grams of cooling agent (WS-3 commercially available from Millennium Specialty Chemicals, of Jacksonville, Fla.) is mixed into the melt by hand with a glass rod. The cooling agent/wax mixture is poured into the aqueous solution and the dispersion and 300 grams of a fruity flavor (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube 4n-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 10% Cooling agent encapsulated in the solid hydrophobic nano-spheres. The controlled release system obtained contains 10% cooling agent, 15% candelilla wax, 30% fruity flavor, and 45% water sensitive material.

EXAMPLE 3

The following procedure is used for the preparation of a controlled release system that provides fragrance transition powder floral to mint) as well as delivers jojoba oil for extended period of time. Menthol and jojoba oil are encapsulated in the hydrophobic nano-spheres and a powder floral fragrance is encapsulated in the water sensitive micro-sphere. The nano-spheres hydrophobic matrix is Ganex® V-220 (commercially available from the ISP Technologies Inc, of Wayne, N.J.). The micro-sphere water sensitive matrix is Hi-Cap™ 100 (commercially available from the National Starch and Chemical Company of Bridgewater, N.J.).

150 grams of Ganex® V-220 (commercially available from the ISP Technologies Inc, of Wayne, N.J.) is placed in an oven at 60 degrees C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. Ganex® V-220 is removed from the oven and 50 grams of Menthol (commercially available from Noville Inc. of South-Hackensack, N.J.) and is 50 grams of jojoba oil (commercially available from JEEN International Corporation of Little Fall, N.J.) are mixed into the melt by hand with a glass rod. The menthol/jojoba oil/Ganex® V-220 mixture is poured into the aqueous solution and the dispersion and 300 grams of a powder floral fragrance (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 5% menthol and 5% jojoba oil encapsulated in the solid hydrophobic nano-spheres. The controlled release system obtained contains 5% menthol and 5% jojoba oil, 15% Ganex® V-220, 30% powder floral fragrance, and 45% water sensitive material.

EXAMPLE 4

The following procedure is used for the preparation of a controlled release system that encapsulates the same fragrance in both the solid hydrophobic nano-spheres and the water sensitive micro-sphere to provide both fragrance "burst" in response to moisture as well as extend fragrance release over a prolog period of time. The nano-spheres hydrophobic matrix is Ganex® V-220 (commercially available from the ISP Technologies Inc, of Wayne, N.J.). The micro-sphere water sensitive matrix is Hi-Cap™ 100 (commercially available from the National Starch and Chemical Company of Bridgewater, N.J.).

250 grams of Ganex® V-220 (commercially available from the ISP Technologies Inc, of Wayne, N.J.) is placed in an oven at 60 degrees ° C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. Ganex® V-220 is removed from the oven and 100 grams of green fragrance (commercially available from Noville Inc. of South-Hackensack, N.J.) is mixed into the melt by hand with a glass rod. The fragrance/Ganex® V-220 mixture is poured into the aqueous solution and the dispersion and 200 grams of a green fragrance (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 10% green fragrance encapsulated in the solid hydrophobic nano-spheres. The controlled release system obtained contains 10% green fragrance in the nano-spheres, 25% Ganex® V-220, 20% green fragrance in the micro-spheres, and 45% water sensitive material.

INCORPORATION OF THE CONTROLLED RELEASE SYSTEM IN LIP BALM PRODUCTS

EXAMPLE 5

The performance of a lip balm comprising the flavor controlled release system of Example 2 (i.e., the ability to yield a high impact flavor "burst" upon wetting the lips, provide flavor transition, and ability to prolong flavor perception on the lips over an extended period of time) was evaluated. The unflavored lip balm base was a commercial ChapStick® unscented lip balm, commercially available from Whitehall-Robins a division of American Home Products Corporation that is flavor free.

A lip balm comprising the controlled release system of the present invention is prepared by weighting 95 grams of the unscented ChapStick® base into ajar following by adding 5 grams of the powder of example 2. The powder is mixed well with the melt and then poured into a lip stick container and allowed to cool for an hour.

The lip balm is applied on the lips and flavor intensity is evaluated after wetting the lips. Flavor transition is clearly noticed after wetting the lips from the initial fruity flavor to a cooling sensation. The cooling sensation was felt for 3 hours after application of the product.

INCORPORATION OF THE CONTROLLED RELEASED SYSTEM IN UNDERARM PRODUCTS

EXAMPLE 6

The performance of an antiperspirant product comprising the fragrance controlled release system of Example 4 (i.e., the ability to yield a high impact fragrance "burst" upon perspiration and ability to prolong fragrance release on the skin over an extended period of time) was evaluated and compared to the performance of the same product comprising the neat fragrance, at the same fragrance level. The unfragranced antiperspirant base was a commercial Degree® unscented antiperspirant stick available from Helene Curtis Company of Chicago, Ill. that is fragrance free.

The antiperspirant sticks were prepared at a 1% effective fragrance concentration using the fragrance described in Example 4. The control sample was prepared by weighting into a jar 1 gram of the neat fragrance and 99 grams of the unscented Degree® and the resulting mixture was melted at 80 degree C. and mixed for about one minute. The melt was poured into an underarm container and allowed to cool for an hour. The antiperspirant stick comprising the controlled release system of the present invention is prepared by weighting 96.7 grams of the unscented Degree® base into ajar following by adding 3.3 grams of the powder of example 4 into the melt. The melt was poured into an underarm container and allowed to cool for an hour.

The antiperspirant samples were applied on the forearm. The ability of the products to provide a "burst" or fragrance transition was evaluated one hour after application of the product by misting the area with water. The products comprising the controlled release system of the present invention was found to provide high impact fragrance "burst" upon wetting the area whereas the control sample comprising the neat oil did not. The forearm areas treated with the antiperspirant comprising the neat fragrance (control) and that treated with the antiperspirant comprising the encapsulated fragrance of example 4 were evaluated for odor intensity after 6 hours and 10 hours. The odor evaluation results were as follow:

|  | Time After Application | |
| --- | --- | --- |
|  | 6 Hours | 10 Hours |
| Neat Fragrance (Control) | 3 | 2 |
| Encapsulated Fragrance | 6 | 5 |

These results show that the forearm treated with the control sample, comprising the neat fragrance, had very low odor intensity. The forearm treated with the antiperspirant comprising the encapsulated fragrance had higher odor intensity. Thus, the controlled release system of the present invention sustains the release of the fragrance over an extended period of time.

INCORPORATION OF THE CONTROLLED RELEASE SYSTEM IN BODY DEODORANT POWDER

EXAMPLE 7

The performance of a deodorant body powder comprising the fragrance controlled release system of Example 3 (i.e., the ability to yield a high impact fragrance "burst" upon perspiration, provide fragrance transition, and ability to prolong fragrance release on the skin over an extended period of time) was evaluated and compared to the performance of the same product comprising the neat fragrance, at the same fragrance level. The unfragranced body deodorant powder base was unscented Pure-Dent® commercially available from Grain Processing Corporation of Muscatine, Iowa.

The body deodorant powders were prepared at a 1% effective fragrance concentration using the fragrance described in Example 3. The control sample was prepared by weighting into a jar 1 gram of the neat fragrance and 99 grams of the unscented Pure-Dent® powder and mixing the powder well. The body deodorant powder comprising the controlled release system of the present invention is prepared by weighting 96.7 grams of the unscented Pure-Dent® powder into ajar following by adding 3.3 grams of the powder of example 3 following by mixing the powders well.

The body deodorant powders samples were applied on the forearm. The ability of the products to provide a "burst" or fragrance transition was evaluated one hour after application of the product by misting the area with water. The product comprising the controlled release system of the present invention was found to provide high impact fragrance "burst" and odor transition upon wetting the forearm area with water whereas the control sample comprising the neat oil did not.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. An anhydrous composition comprising:
a plurality of solid nano-spheres, each of said solid nano-spheres comprising an effective amount of a first active agent, said plurality of nano-spheres are formed of a hydrophobic material, said hydrophobic material is selected from one or more of the group consisting of natural wax, synthetic wax, vegetable wax, natural wax and silicon copolymer, synthetic wax and silicon copolymer, fatty acid esters, fatty alcohols, solid hydrogenated plant oil, natural polymers and synthetic polymers, said plurality of nano-spheres being encapsulated in a moisture sensitive micro-sphere, said moisture sensitive micro-sphere is formed of a moisture sensitive matrix material, said moisture sensitive micro-sphere comprising a second active agent encapsulated in said moisture sensitive matrix material, said second active agent is the same or different than said first active agent, said first and second active agents being selected from the group consisting of fragrance, flavor, cosmetic agent, dermatological agent and pharmaceutical agent, said moisture sensitive micro-sphere dissolves to release said second active agent and said plurality of nano-spheres upon contact with moisture from the skin or lips to provide a burst of said second active agent and said nano-spheres release said first active agent continuously thereafter for an extended period of time or said micro-sphere swells or softens upon contact with moisture from the skin or lips to slowly release said second active agent and said nanospheres and said nano-spheres release said first active agent continuously thereafter for an extended period of time in the range of a day to a few weeks.

2. The composition of claim 1 wherein said hydrophobic material is selected from the group consisting of alkylated polyvinyl pyrolidine, hydrogenated castor oil, hydrenated vegtable oil, hard paraffin, hard fat and triglyceride.

3. The composition of claim 1 wherein said polyvinyl alcohol has a degree of hydrolysis from about 75% to about 99%.

4. The composition of claim 1 wherein said first active agent comprises one or more agents selected from the group consisting of: anti-oxidants; free radical scavengers; moisturizers; depigmentation agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants; poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; and skin penetration enhancers.

5. The composition of claim 1 wherein said first active agent is present in about 1% to about 80% by weight of said nano-spheres.

6. The composition of claim 1 wherein said first active agent is present in about 1% to about 80% by weight of said nano-spheres and said second active agent is present in about 0.01% to about 60% by weight of said nano-sphere.

7. The composition of claim 1 wherein said micro-sphere has a size of from about 2.0 to about 100 microns.

8. The composition according to claim 1 wherein each of said nano-spheres has an average size of about 0.01 to about 5 microns.

9. A anhydrous cosmetic composition comprising a plurality of solid nano-spheres comprising a first active agent, said plurality of nano-spheres are formed of a hydrophobic material, said hydrophobic material is selected from one or more of the group consisting of natural wax, synthetic wax, vegetable wax, natural wax and silicon copolymer, synthetic wax and silicon copolymer, fatty acid esters, fatty alcohols, solid hydrogenated plant oil, natural polymers and synthetic polymers, said plurality of nano-spheres being encapsulated in a moisture sensitive micro-sphere, said moisture sensitive micro-sphere is formed of a moisture sensitive matrix material, said moisture sensitive matrix material is formed of about 1% to about 80% polyvinyl alcohol and about 1% to about 80% polysaccharide by weight of the matrix material, said moisture sensitive micro-sphere comprising a second active agent encapsulated in said moisture sensitive matrix material, said second active agent is the same or different than said first active agent, said first and second active agents being selected from the group consisting of: fragrance, flavor, cosmetic agent, dermatological agent and pharmaceutical agent, said moisture sensitive micro-sphere dissolves to release said second active agent and said plurality of nano-spheres upon contact with moisture from the skin or lips to provide a burst of said second active agent and said nano-spheres release said first active agent continuously thereafter for an extended period of time or said micro-sphere swells or softens upon contact with moisture from the skin or lips to slowly release said second active agent and said nano-spheres, and said nano-spheres release said first active agent continuously thereafter for an extended period of time in the range of a day to a few weeks.

10. A spray product comprising the composition of claim 9.

11. The spray product of claim 10 wherein said first active agent or said second active agent comprises one or more agents selected from the group consisting of: anti-oxidants; free radical scavengers; moisturizers; depigmentation agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterritants; poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; and skin penetration enhancers.

12. The spray product of claim 10 wherein said spray product is a deodorant, antiperspirant, body spray, foot spray, hygiene spray, feminine napkin spray or undergarment spray.

13. A powder product comprising the composition of claim 9.

14. The powder product of claim 13 wherein said first active agent comprises one or more agents selected from the group consisting of: anti-oxidants; free radical scavengers; moisturizers; depigmentation agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants; poison ivy agents; poison oak agents; burn products; make-up preparations; vitamins; amino acids and their derivatives; herbal extracts; cooling agents; heating agents, etc.); skin conditioners; chelating agents; cell turnover enhancers; coloring agents; sunscreens; nourishing agents; moisture absorbers; sebum absorbers; and skin penetration enhancers.

15. The powder product of claim 13 wherein said powder product is a deodorant body powder.

16. A stick product comprising the composition of claim 9.

17. The stick product of claim 16 wherein said first active agent comprises one or more agents selected from the group consisting of: anti-oxidants; free radical scavengers; moisturizers; depigmentation agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants; poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; and skin penetration enhancers.

18. The stick product of claim 16 wherein said stick product is a lip balm, lipstick, makeup stick, underarm deodorant stick or underarm antiperspirant stick.

19. A method for forming the composition of claim 1 comprising the steps of:

heating one or more hydrophobic materials to a temperature above the melting point of the materials to form a melt;

dissolving or dispersing the first active agent into the melt;

dissolving or dispersing a second active agent and said moisture sensitive matrix material in the aqueous phase to form an aqueous composition;

heating the aqueous composition to above the melting temperature of the hydrophobic materials to form a hot melt;

mixing the hot melt with the aqueous phase to form a dispersion;

high shear homogenization of the dispersion at a temperature above the melting temperature until a homogeneous fine dispersion is obtained having a sphere size of from about 1 micron to about 2 microns;

cooling the dispersion to ambient temperature; and spray drying the emulsified mixed suspension to form a dry powder composition.

* * * * *